(12) United States Patent
Sumpf et al.

(10) Patent No.: US 10,855,923 B2
(45) Date of Patent: Dec. 1, 2020

(54) METHOD AND DEVICE FOR ACQUIRING AND DISPLAYING AN IMMUNOFLUORESCENCE IMAGE OF A BIOLOGICAL SAMPLE

(71) Applicant: EUROIMMUN Medizinische Labordiagnostika AG, Luebeck (DE)

(72) Inventors: Tilman Johannes Sumpf, Luebeck (DE); Michael Pape, Luebeck (DE); Martin Hagen-Eggert, Luebeck (DE); Christian Piepke, Luebeck (DE); Thomas Laudan, Kiel (DE); Michael Falkert, Reinfeld (DE); Markus Morrin, Luebeck (DE); Kristin Rentzsch, Bad Schwartau (DE)

(73) Assignee: EUROIMMUN Medizinische Labordiagnostika AG, Luebeck (DE)

( * ) Notice: Subject to any disclaimer, the term of this patent is extended or adjusted under 35 U.S.C. 154(b) by 0 days.

(21) Appl. No.: 16/569,772

(22) Filed: Sep. 13, 2019

(65) Prior Publication Data

US 2020/0092478 A1    Mar. 19, 2020

(30) Foreign Application Priority Data

Sep. 13, 2018 (EP) .................................... 18194332

(51) Int. Cl.
*G01N 15/14* (2006.01)
*G02B 21/36* (2006.01)
(Continued)

(52) U.S. Cl.
CPC ..... *H04N 5/23245* (2013.01); *G01N 21/6458* (2013.01); *G01N 33/4833* (2013.01);
(Continued)

(58) Field of Classification Search
CPC ........ G01N 21/00; G01N 21/64; G01N 21/62; G01N 21/63; G01N 21/84; G01N 21/8901;
(Continued)

(56) References Cited

U.S. PATENT DOCUMENTS 9,250,434 B2    2/2016  Morrin
2006/0178833 A1*  8/2006  Bauer ................ G01N 15/1475
                                                    702/19
2013/0162804 A1   6/2013  Morrin

FOREIGN PATENT DOCUMENTS

DE    10 2006 027 518    12/2007
EP          2 000 842      12/2008
(Continued)

OTHER PUBLICATIONS

Extended European Search Report dated Jan. 14, 2019 in European Application No. 18194332.5 with English Translation.

*Primary Examiner* — Don K Wong
(74) *Attorney, Agent, or Firm* — Grüneberg and Myers PLLC

(57) ABSTRACT

A method is used for acquiring and displaying an immunofluorescence image of a biological sample. During a first operating state, the sample is continuously illuminated using the excitation radiation. A relative position between the sample and an optical system, which guides the fluorescent radiation to an image sensor, is changed in dependence on a movement gesture of a user, and a corresponding digital image is displayed. Upon detection of a termination of the movement gesture, a change is made from the first operating state to a second operating state. In the second operating state, the sample is firstly illuminated using the excitation radiation to excite the fluorescent radiation of the fluorescent pigment. An acquisition of fluorescent radiation emitted by the sample then takes place and a corresponding, further (Continued)

digital image is generated. In the second operating state, the acquisition of the emitted fluorescent radiation and the illumination of the sample are terminated after lapse of the second acquisition duration.

20 Claims, 10 Drawing Sheets

(51) Int. Cl.
    *H04N 5/232*     (2006.01)
    *G01N 21/64*     (2006.01)
    *G01N 33/483*     (2006.01)
    *G02B 21/16*     (2006.01)
    *G02B 21/26*     (2006.01)
    *H04N 5/225*     (2006.01)

(52) U.S. Cl.
    CPC ............ *G02B 21/16* (2013.01); *G02B 21/26* (2013.01); *G02B 21/36* (2013.01); *H04N 5/2256* (2013.01); *H04N 5/23219* (2013.01)

(58) Field of Classification Search
    CPC ....... G01N 21/6486; G01N 2021/6491; G01N 21/6426; G01N 21/6456; G01N 21/6458; G01N 2021/646; G01N 2021/6458; G01N 21/6482; G01N 33/4833; G01N 33/00; G01N 33/483; G01N 21/6489
    See application file for complete search history.

(56) References Cited

FOREIGN PATENT DOCUMENTS

| | | |
|---|---|---|
| EP | 2 557 446 | 2/2013 |
| EP | 2 690 482 | 1/2014 |
| EP | 3 418 789 | 12/2018 |
| EP | 18214781.9 | 12/2018 |
| JP | H08-223563 | 8/1996 |

* cited by examiner

Fig. 8b BI2
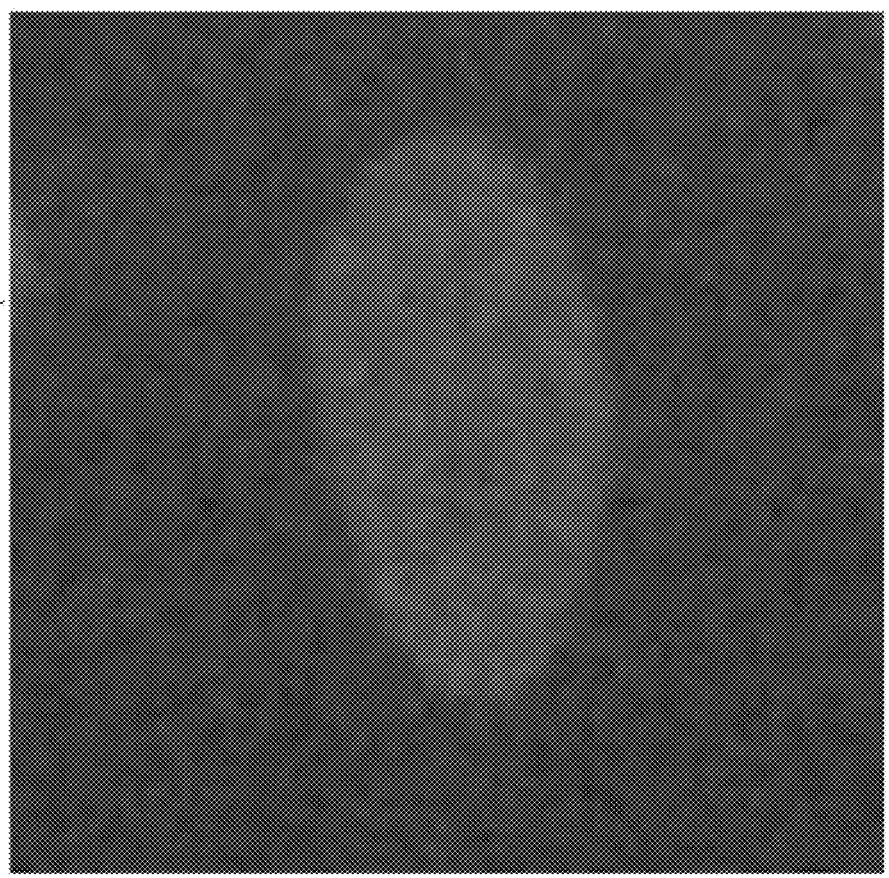
Fig. 8a BI1

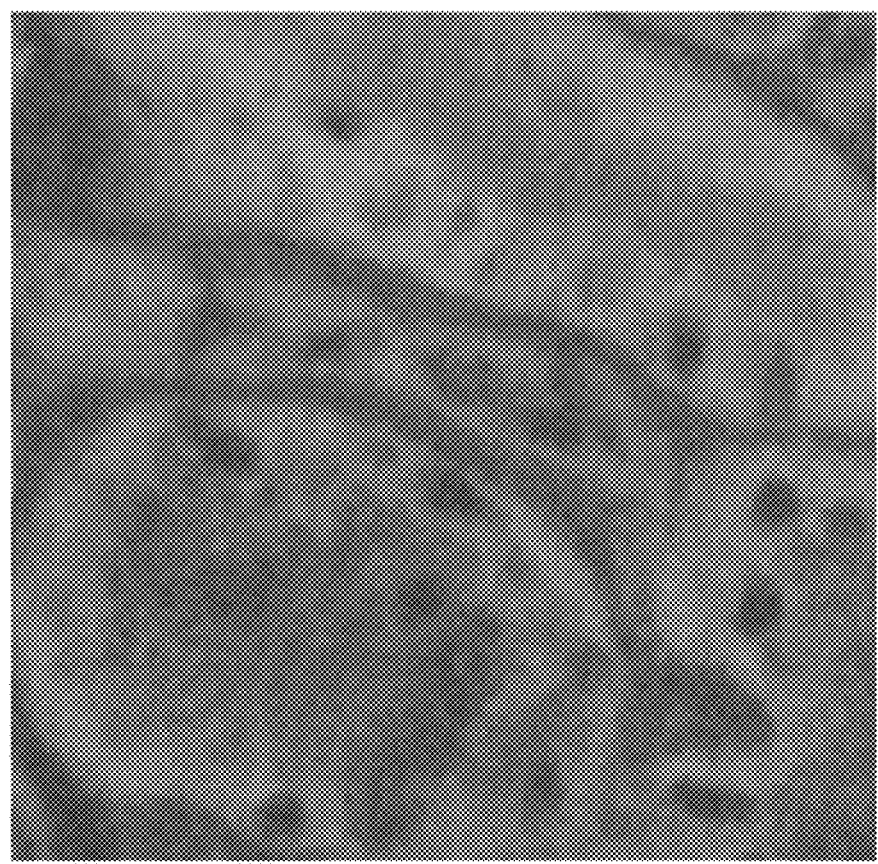
Fig. 10b  BI12
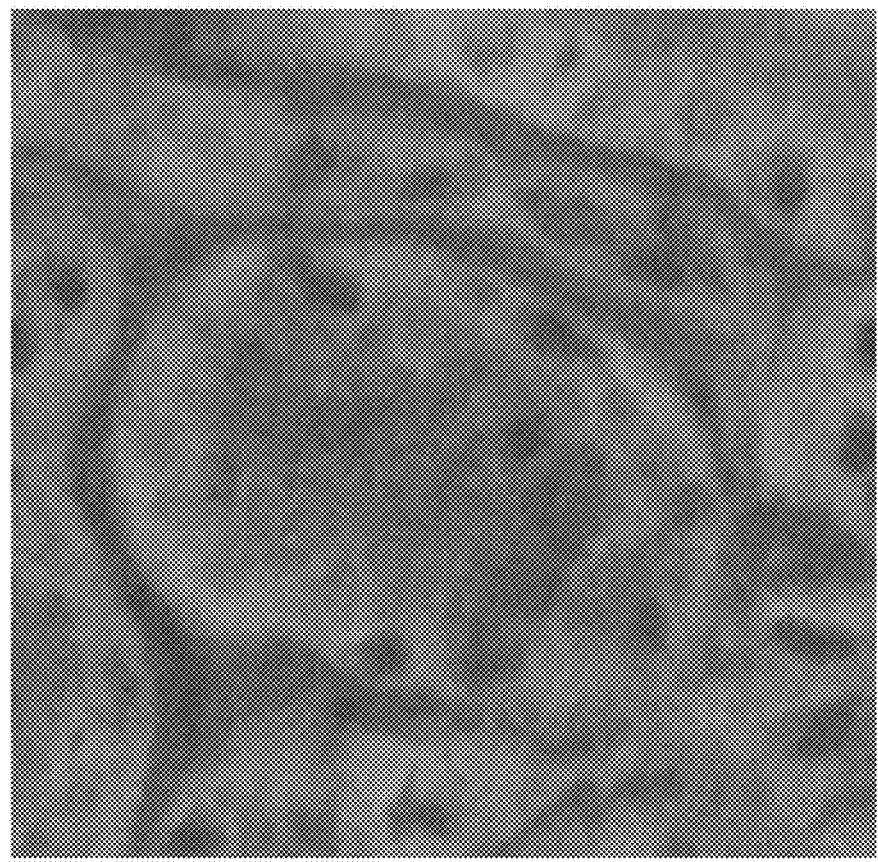
Fig. 10a  BI11

METHOD AND DEVICE FOR ACQUIRING AND DISPLAYING AN IMMUNOFLUORESCENCE IMAGE OF A BIOLOGICAL SAMPLE

CROSS-REFERENCE TO RELATED APPLICATIONS

The present application claims the benefit of the European Application EP18 194 332.5, filed on Sep. 13, 2018, which is incorporated by reference in its entirety.

BACKGROUND OF THE INVENTION

Field of the Invention

Methods and devices are known from the related art for acquiring so-called immunofluorescence images of biological samples by means of image sensors and displaying them on display units.

Discussion of the Background

Such a biological sample is, for example, a tissue sample, which has been taken from a human or animal. In the course of so-called direct immunofluorescence, for example, cell components within the tissue can be made visible by incubating the tissue with antibodies of a defined type, wherein the antibodies specifically react with defined antigens of the tissue. In this case, so-called fluorescent pigments are bonded to the antibodies, such that the structures to be detected can then be made visible in an immunofluorescence image. For this purpose, the fluorescent pigment is irradiated using an excitation light of a defined excitation wavelength, such that the fluorescent radiation, which has a different wavelength than the excitation wavelength, is then emitted from the tissue and can be guided by means of an objective lens onto an image sensor to then be acquired by the image sensor.

In the course of so-called indirect immunofluorescence, for example, a tissue, for example, monkey liver, is used as the biological sample and incubated with a blood serum of a patient in a first incubation step to detect possible bonding of antibodies in the serum of the patient on defined antigens of the tissue. Furthermore, a second incubation using antibodies of a second type is also carried out, which then bond to the first antibody from the blood serum, wherein the second antibody is also again marked using a fluorescent pigment. The incubated tissue is then also irradiated using the excitation light of the excitation wavelength in indirect immunofluorescence, such that bonding of antibodies of the patient to defined antigens in the tissue becomes visible due to a fluorescent radiation of the fluorescent pigment having a fluorescence wavelength which differs from the excitation light wavelength.

The biological sample can also be provided by so-called antigen spots, which have antibodies of the patient bonded to the antigen spots after incubation of the antigen spots with a blood serum of a patient. So-called second antibodies, which are in turn marked with a fluorescent pigment, can then be bonded on the antibodies of the patient in turn after carrying out a further incubation step.

Immunofluorescence images obtained in this manner can then be the subject matter of a clinical finding.

Devices are known in particular, for example, microscopes, in which a user can manually perform an alignment of the sample in relation to the microscope or the objective lens of the microscope to make visible in the obtained immunofluorescence image a defined region or a defined detail of the sample.

SUMMARY OF THE INVENTION

The object of the present invention is to provide a device and a method for a user, in the case of which an acquisition of immunofluorescence images on different details or regions of a sample is made as simple as possible for a user and able to be handled and/or operated well and carried out reliably.

The object according to the invention is achieved by a method according to embodiment 1 and a device according to embodiment 13.

The present invention includes the following embodiments:

1) Method for acquiring and displaying an immunofluorescence image (BI1, BI2, BI3) of a biological sample (G),
    comprising in a first operating state (BZ1)
        continuously illuminating the sample (G) using excitation radiation (AS),
        changing a relative position between the sample (G) and an optical system (OS), which guides fluorescent radiation (FS) emitted by the sample (G) onto at least one image sensor (BS), in dependence on a movement gesture (BG1) of a user,
        acquiring the fluorescent radiation (FS) by means of multiple sensor pixels (P1, P2, P3, P4, P5, P6, P7, P8, P9, P10, P11, P12, P13, P14) of the at least one image sensor (BS) using a first acquisition duration and determining a digital image (BI1, BI2), and
        displaying the digital image (BI1, BI2),
    wherein in the first operating state (BZ1), the acquisition of the fluorescent radiation (FS) as well as the determination and the display of the digital image (BI1, BI2) are repeated at successive points in time at a defined repetition frequency,
    wherein furthermore upon detection of a termination of the movement gesture (BG1), a change is made from the first operating state (BZ1) to a second operating state (BZ2),
    furthermore comprising in a second operating state (BZ2)
        illuminating the sample (G) using the excitation radiation (AS),
        acquiring fluorescent radiation (FS) emitted by the sample (G) by means of the multiple sensor pixels (P1, P2, P3, P4, P5, P6, P7, P8, P9, P10, P11, P12, P13, P14) using a second acquisition duration and determining a further digital image (BI3),
        displaying the further digital image (BI3),
        terminating the acquisition of the emitted fluorescent radiation (FS) and terminating the illumination of the sample (G) after lapse of the second acquisition duration,
        continuously displaying the further digital image (BI3) after the termination of the acquisition of the fluorescent radiation (FS) and the termination of the illumination of the sample (G).

2) Method according to embodiment 1,
    wherein the second acquisition duration is greater than the first acquisition duration.

3) Method according to embodiment 1,
furthermore comprising
terminating the second operating state (BZ2) and changing to the first operating state (BZ1) upon detection of a beginning of a new movement gesture (BG2) of the user.
4) Method according to embodiment 1,
wherein the digital image (BI1, BI2) in the first operating state (BZ1) and the further digital image (BI3) in the second operating state (BZ2) are determined such that at equal light intensity of the fluorescent radiation (FS), the digital image (BI1, BI2) of the first operating state (BZ1) and the further digital image (BI3) of the second operating state (BZ2) have an equal intensity.
5) Method according to embodiment 4,
wherein the digital image (BI1, BI2) in the first operating state (BZ1) and the further digital image (BI3) in the second operating state (BZ2) are determined such that at equal light intensity of the fluorescent radiation (FS), the digital image (BI1, BI2) of the first operating state (BZ1) and the further digital image (BI3) of the second operating state (BZ2) have an equal intensity, by one or more of the following parameters being chosen differently for the first operating state (BZ1) and for the second operating state (BZ2):
amplification factor for sensor pixel values (SW),
number of sensor pixel values (SW) which are combined by means of binning to form one image pixel value,
number of sensor pixel values (SW) which are combined by means of debayering to form one image pixel value.
6) Method according to embodiment 1,
wherein the digital image (BI1, BI2) is determined in the first operating state (BZ1) such that it has a first image resolution,
wherein the further digital image (BI3) is determined in the second operating state (BZ2) such that it has a second image resolution,
and wherein the first image resolution is chosen smaller than the second image resolution.
7) Method according to embodiment 1,
wherein in the second operating state (BZ2), the acquisition of the emitted fluorescent radiation (FS) is carried out using multiple successive partial acquisition durations within the second acquisition duration,
wherein corresponding temporary digital images are determined for the partial acquisition durations,
and wherein the further digital image (BI3) is determined on the basis of the temporary digital images.
8) Method according to embodiment 7,
wherein in the second operating state (BZ2), upon detection of a beginning of a new movement gesture (BG2) of the user, the acquisition of the emitted fluorescent radiation (FS) and the determination of the temporary digital images is terminated and a transition is made into the first operating state (BZ2).
9) Method according to embodiment 1,
wherein a colour image sensor (BS1) is used as the image sensor (BS).
10) Method according to embodiment 1,
wherein a greyscale image sensor (BS2), which detects fluorescent radiation (FS2) in a green channel, is used as the image sensor (BS).
11) Method according to embodiment 10,
wherein furthermore a further greyscale image sensor (BS3) is used, which detects fluorescent radiation (FS3) in a red channel.
12) Method according to embodiment 1,
wherein upon a change from the first operating state (BZ1) to the second operating state (BZ2), before reaching the second operating state (BZ2), a focusing of the optical system (OS) on the sample (G) is carried out.
13) Device (V) for acquiring and displaying an immunofluorescence image (BI1, BI2, BI3) of a biological sample (G),
comprising
an excitation light source (AL) for illuminating the sample (G) using excitation radiation (AS),
a holding device (H) for holding the sample (G),
at least one image sensor (BS) having multiple sensor pixels (P1, P2, P3, P4, P5, P6, P7, P8, P9, P10, P11, P12, P13, P14) for acquiring fluorescent radiation (FS) emitted by the sample (G),
an optical system (OS) for guiding the fluorescent radiation (FS) from the sample (G) onto the image sensor (BS),
a positioning unit (P), which is designed to change a relative position between the sample (G) and an optical system (OS),
at least one control unit (S) having a first interface (SC1) to a user input device (N), a second interface (SC2) to the image sensor (BS), a third interface (SC3) to the excitation light source (AL), a fourth interface (SC4) to the positioning unit (P), and a fifth interface (SC5) to a display unit (AE),
wherein the control unit (S) is designed, in a first operating state (BZ1)
to control the excitation light source (AL) in such a way that the sample (G) is continuously illuminated using the excitation radiation (AS),
furthermore to derive a movement gesture (BG1) of the user from an input signal (ES) of the user input device (N) and to control the positioning unit (P) in such a way that the relative position between the sample (G) and the optical system (OS) is changed in dependence on the movement gesture (BG1),
to control the image sensor (BS) in such a way that, by means of the multiple sensor pixels (P1, P2, P3, P4, P5, P6, P7, P8, P9, P10, P11, P12, P13, P14), the fluorescent radiation (FS) is acquired using a first acquisition duration and furthermore to determine a digital image (BI1, BI2) from resulting sensor pixel values (SW) and also furthermore
to control the display unit (AE) to display the digital image (BI1, BI2),
wherein the control unit (S) is furthermore designed, in the first operating state (BZ1)
to repeat the acquisition of the fluorescent radiation (FS) as well as the determination and the display of the digital image (BI1, BI2) at successive points in time using a defined repetition frequency
and upon detection of a termination of the movement gesture (BG1), to change to a second operating state (BZ2),
wherein the control unit (S) is furthermore designed, in the second operating state (BZ2)
to control the image sensor (BS) so that by means of the multiple sensor pixels (P1, P2, P3, P4, P5, P6, P7, P8, P9, P10, P11, P12, P13, P14), the fluorescent radiation (FS) is acquired using a second acquisition duration and furthermore to determine a further digital image (BI3) from resulting sensor pixel values (SW), and to control the display unit (AE) to display the further digital image (BI3), and furthermore to control the image sensor (BS) so that after lapse of the second acquisition duration, the acquisition of the fluorescent radiation (FS) is terminated, and also furthermore to control the excitation light source (AL) in such a way that the illumination of the sample (G) is terminated after lapse of the second acquisition duration, and finally furthermore to control the display unit (AE) after the termination of the illumination of the sample (G) and after the termination of the acquisition of the emitted fluorescent radiation (FS) in such a way that the further digital image (BI3) is continuously displayed.

14) Device according to embodiment 13,
wherein the second acquisition duration is greater than the first acquisition duration.

15) Device according to embodiment 13,
wherein the control unit (S) is furthermore designed, upon detection of a beginning of a new movement gesture (BG2) of the user, to end the second operating state (BZ2) and to change to the first operating state (BZ1).

BRIEF DESCRIPTION OF DRAWINGS

FIG. 8a shows a first image detail BI1 in which so-called HEP cells (human epithelial cells) are shown. This image was obtained during a first operating state using the device according to the invention.

FIG. 8b shows an image detail BI2.

FIG. 10a shows an image detail of an immunofluorescence image of a tissue during the first operating state.

FIG. 10b shows an image detail of an immunofluorescence image of a tissue during the first operating state.

DETAILED DESCRIPTION OF THE INVENTION

Figure 1:
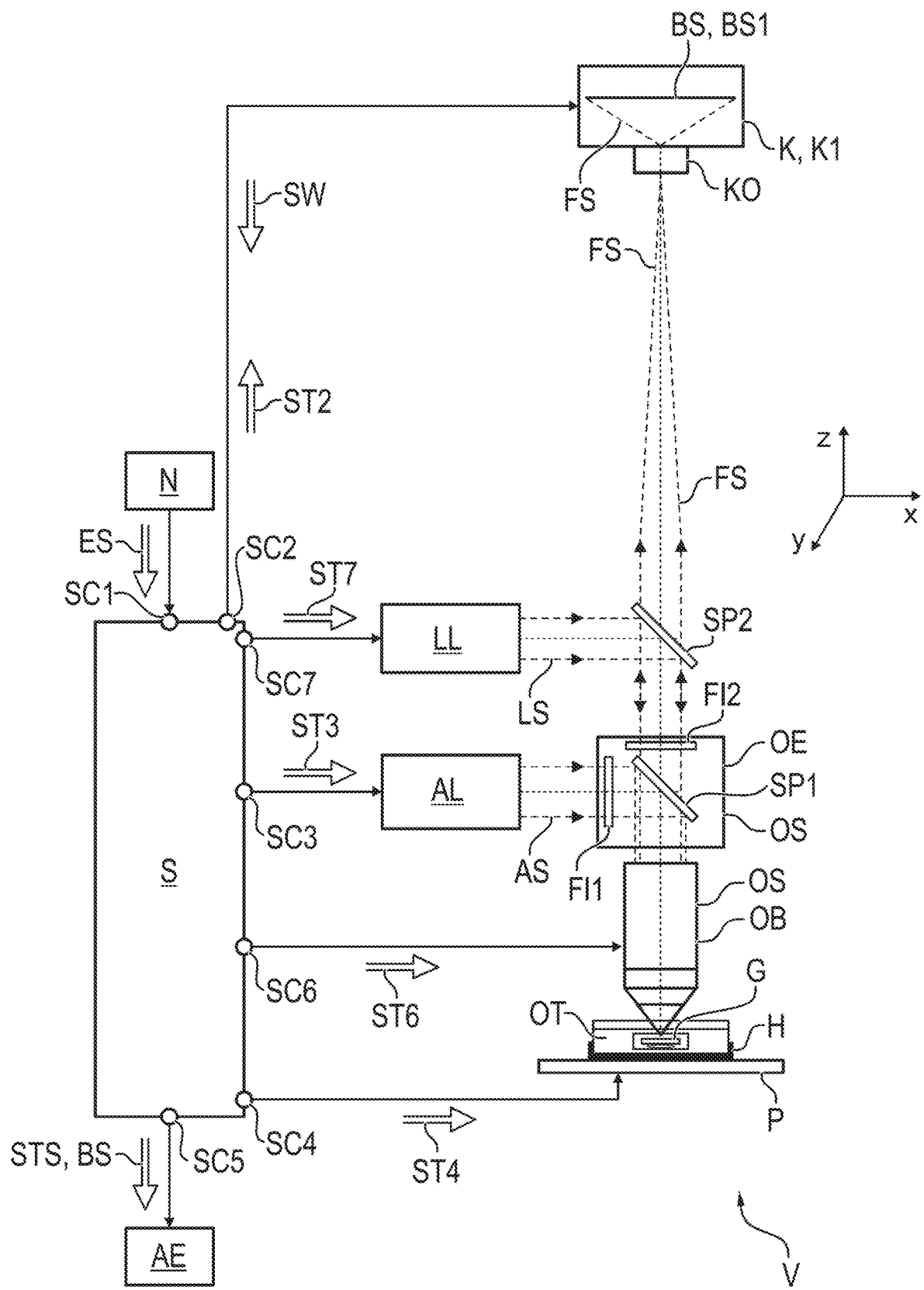
FIG. 1 shows one preferred embodiment of the device according to the invention.

A method is proposed for acquiring and displaying an immunofluorescence image of a biological sample. In a first operating state, the method carries out defined method steps. During the first operating state, the sample is continuously illuminated using the excitation light. In this way, in particular a continuous emission of the fluorescent radiation by the sample is generated. A relative position between the sample and an optical system, which guides fluorescent radiation emitted by the sample onto at least one image sensor, is changed in dependence on a movement gesture of a user. In this way, in particular the user can determine by movement gestures which detail of the sample is made visible by means of the optical system and the image sensor in the immunofluorescence image. During the first operating state, the fluorescent radiation is acquired by means of multiple sensor pixels of at least one image sensor using a first acquisition duration. A digital image is then determined on the basis of the resulting sensor pixel values of the sensor pixels and this digital image is displayed.

In the first operating state, the acquisition of the fluorescent radiation as well as the determination and the display of the digital image are repeated at successive points in time at a defined repetition frequency. In this way, in particular in the case in which a movement gesture is carried out continuously, different details or regions of the sample are thus in each case acquired in the immunofluorescence image and displayed in the digital image at the respective corresponding, successive points in time. The user can thus determine in particular by carrying out the movement gesture which detail of the sample is represented and/or displayed in the digital image. In this case, the acquisition of the fluorescent radiation for a digital image of a point in time having the first acquisition duration takes place in particular in the first operating state. The maximum repetition frequency for the representation of the successive digital images in the first operating state is thus determined in particular by this first acquisition duration and is the reciprocal value of the first acquisition duration.

Upon detection of a termination of the movement gesture, a change is made from the first operating state to a further, second operating state. In the second operating state, the sample is firstly illuminated using the excitation light to excite the fluorescent radiation of the fluorescent pigment. An acquisition of fluorescent radiation emitted by the sample then takes place by means of the multiple sensor pixels using a second acquisition duration. This second acquisition duration is preferably greater than the first acquisition duration. A further digital image is then generated on the basis of resulting sensor pixel values of the sensor pixels. In the second operating state, the acquisition of the emitted fluorescent radiation and the illumination of the sample are terminated after lapse of the second acquisition duration. Furthermore, the further digital image is continuously displayed after the termination of the acquisition of the fluorescent radiation and the termination of the illumination of the sample.

To explain one advantage or multiple advantages which can possibly be achieved by the invention more accurately to the reader, further detailed explanations follow hereafter. It is necessary for a user, for example, for an actual finding of a patient, to observe not only one image detail of an incubated sample in an immunofluorescence image, but rather to be able to observe various regions of a tissue in a high magnification level in each case. For this purpose, the user has to be able to change a relative position of the optical system, which guides the emitted fluorescent radiation from tissue onto the image sensor, in relation to the sample. In particular in the case of a high optical enlargement, the user desires to be able to observe such different regions, possibly in higher image quality, if the relative position between the sample and the optical system remains unchanged, such that during the second operating state, the same image detail of the sample is consistently displayed in the form of the further digital image. The user possibly desires to observe the displayed further digital image for a longer time, to observe structures or colourations in greater detail and decide for himself whether he possibly desires to observe another image detail by inputting a further movement gesture. Because the further digital image is continuously displayed in the second operating state after the lapse of the second acquisition duration, and furthermore the illumination of the sample by the excitation radiation is terminated, so-called burnout of the biological sample because of illumination using the excitation radiation is minimized. If the sample were continuously illuminated using the excitation radiation during the second operating state, the sample would thus burn out significantly earlier and would no longer be usable for microscopy, which is to be considered a technical problem. The impression results for the user by way of the method proposed here that he not only has images acquired continuously during the performance of his movement gesture displayed as representation of a real microscopic image, but rather also a continuous microscopic image is also displayed to him during the second operating state, since he has the further digital image continuously displayed. By way of the solution proposed here, the user thus receives the impression of continuous microscopy or so-called "live microscopy" on the display unit, although during the second operating state after lapse of the second acquisition duration and after the determination of the further digital image, no further acquisition of fluorescent radiation with simultaneous illumination of the tissue using the excitation radiation takes place. The user thus does not notice at all that image acquisition no longer occurs at all during at least a chronological subsection of the second operating state, and the biological sample is nonetheless simultaneously protected with respect to a burnout.

A further technical problem is that the user, on the one hand, while carrying out a movement gesture, for example, by stroking a finger on a touch-sensitive display surface such as a touchscreen, expects the most flowing possible image or judder-free image in the display on the display unit to have the feeling that the image detail and/or the positioning unit follows his movement gesture without delay and he does not have the impression due to a delayed display of digital images obtained at successive points in time that the image acquisition device chooses the image detail and displays the digital images with delay. At the same time, however, it is necessary for the user that after carrying out his movement gesture and the selection accompanying this of a defined image detail of the sample, in the second operating state, he has the further digital image displayed in sufficient and/or relatively high quality, since in immunofluorescence images, ultrasmall image details can be of interest for the finding by the user. Since an emitted fluorescent radiation only has a certain optical power and/or certain optical intensity per unit of area, but at the same time image sensors can only acquire a defined quantity of light at a given pixel resolution and/or a given area per sensor pixel at a defined acquisition time or exposure time, a so-called sensor noise has an effect on the image signal to a certain degree depending on chosen acquisition duration and given pixel resolution. For example, if an acquisition duration having a relatively high value of, for example, 500 ms were chosen, a certain quantity of light of the fluorescent radiation could be collected during this acquisition duration at each individual sensor pixel and the useful signal of the image obtained here could therefore overlap an overlaid noise signal of the sensor and/or the electronics to a sufficient degree. However, in such a case it would also solely be possible to obtain digital images at successive points in time having a time interval of 500 ms from one another, which would not be sufficient for a fluidly appearing display and/or selection of an image detail of the sample in dependence on the movement gesture, since the image frequency would only be 2 images per second.

Because the acquisition duration in the first operating state is preferably chosen smaller than the acquisition duration in the second operating state, the repetition frequency and/or display frequency of the digital images in the first operating state can be chosen high enough to give the user the impression of a fluid and judder-free image in relation to his movement gesture. Furthermore, because the acquisition duration is chosen higher in the second operating state than in the first operating state, the image signal for the further digital image can be obtained in sufficient intensity and the further digital image can thus be displayed in sufficient image quality, such that smaller details are also well recognizable to the user. While a user changes a change of the optical detail of the sample which is displayed in the digital image of the first operating state, by means of the movement gesture, the user solely orients himself on relatively rough structures, to determine for himself whether the chosen detail of the tissue is that which he desires to observe in a higher image quality as a so-called still image. In other words: the user is not interested in obtaining digital images which reflect all details at successive points in time during the performance of his movement gesture in the first operating state, but rather it is sufficient for him if these digital images only have a certain minimum quality. After terminating his movement gesture, however, he requires a higher-quality image to be able to recognize all details accurately. Therefore, in the second operating state for the further digital image, the fluorescent radiation is acquired using the second acquisition duration, which is greater than the first acquisition duration of the first operating state.

If the user carries out the movement gesture, the digital images during the first operating state at the successive points in time are thus displayed to him at only a certain image quality because of the selection of the first acquisition duration. However, it is not actually possible for the human eye and the human brain while a moving image is displayed to completely perceive such a quality difference. The user therefore has the optical impression during the first operating state that the image quality only slightly changes between the first operating state and the second operating state, wherein at the same time because of the solution according to the invention, however, the digital images at the successive points in time during the first operating state are displayed so fluidly and/or judder-free in dependence on his movement gesture that the user does not perceive a noticeable delay between his movement gesture and the change of the relative position between the optical unit and the sample.

Advantages of the further embodiments of the invention are explained in greater detail in the following description, partially with reference to the figures.

Preferably, upon detection of a beginning of a new movement gesture of the user, the second operating state is terminated and a transition is made into the first operating state.

Preferably, the digital image in the first operating state and the further digital image in the second operating state are determined such that at equal light intensity of the fluorescent radiation, the digital image of the first operating state and the further digital image of the second operating state have an equal intensity.

Preferably, the digital image in the first operating state and the further digital image in the second operating state are determined such that at equal light intensity of the fluorescent radiation, the digital image of the first operating state and the further digital image of the second operating state have an equal intensity, by one or more of the following parameters being chosen differently for the first operating state and for the second operating state:

amplification factor for sensor pixel values,
number of sensor pixel values which are combined by means of binning to form one image pixel value,
number of sensor pixel values which are combined by means of debayering to form one image pixel value.

Preferably, the digital image in the first operating state is determined such that it has a first image resolution, wherein the further digital image is determined in the second operating state so such it has a second image resolution, and wherein the first image resolution is chosen smaller than the second image resolution.

Preferably, in the second operating state, the acquisition of the emitted fluorescent radiation is carried out using multiple successive partial acquisition durations within the second acquisition duration, wherein corresponding temporary digital images are determined for the partial acquisition durations and wherein the further digital image is determined on the basis of the temporary digital images.

Preferably, in the second operating state, upon detection of a beginning of a new movement gesture of the user, the acquisition of the emitted fluorescent radiation and the determination of the temporary digital images is terminated and a transition is made into the first operating state.

Preferably, a colour image sensor is used as the image sensor.

Preferably, a greyscale image sensor, which detects fluorescent radiation in a green channel, is used as the image sensor.

Preferably, a further greyscale image sensor, which detects fluorescent radiation in a red channel, is furthermore used.

Preferably, upon a change from the first operating state to the second operating state, before reaching the second operating state, a focusing of the optical system on the sample is carried out.

Figure 2A:
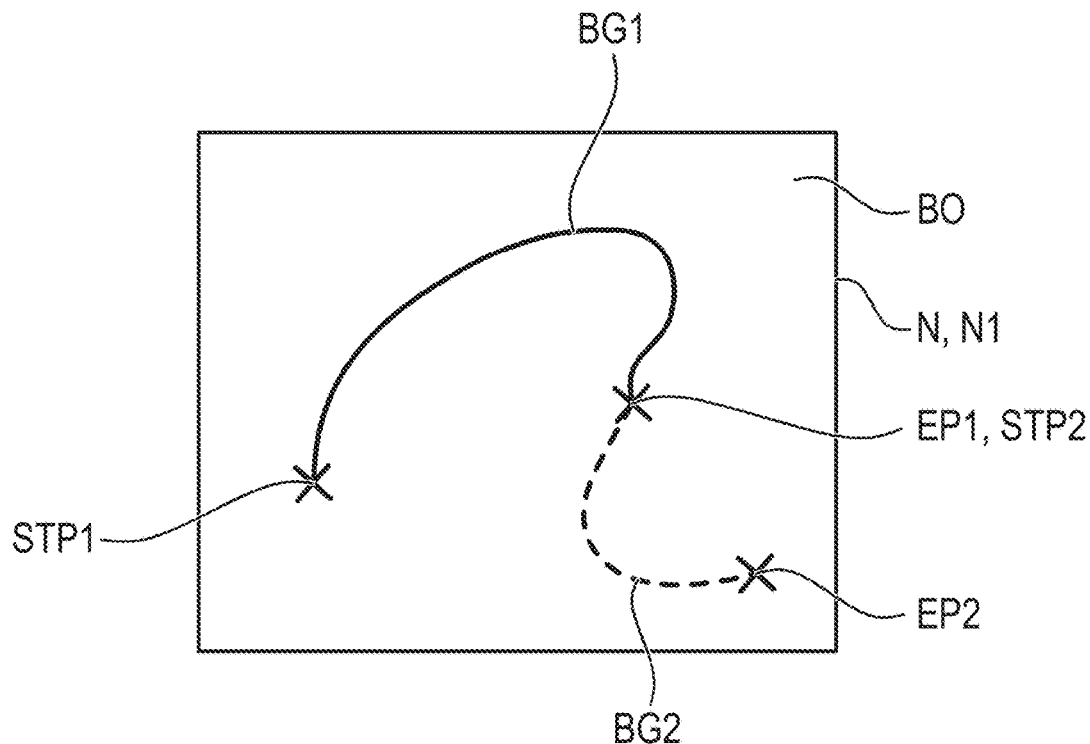
FIG. 2a shows a user input device.
Figure 2B:
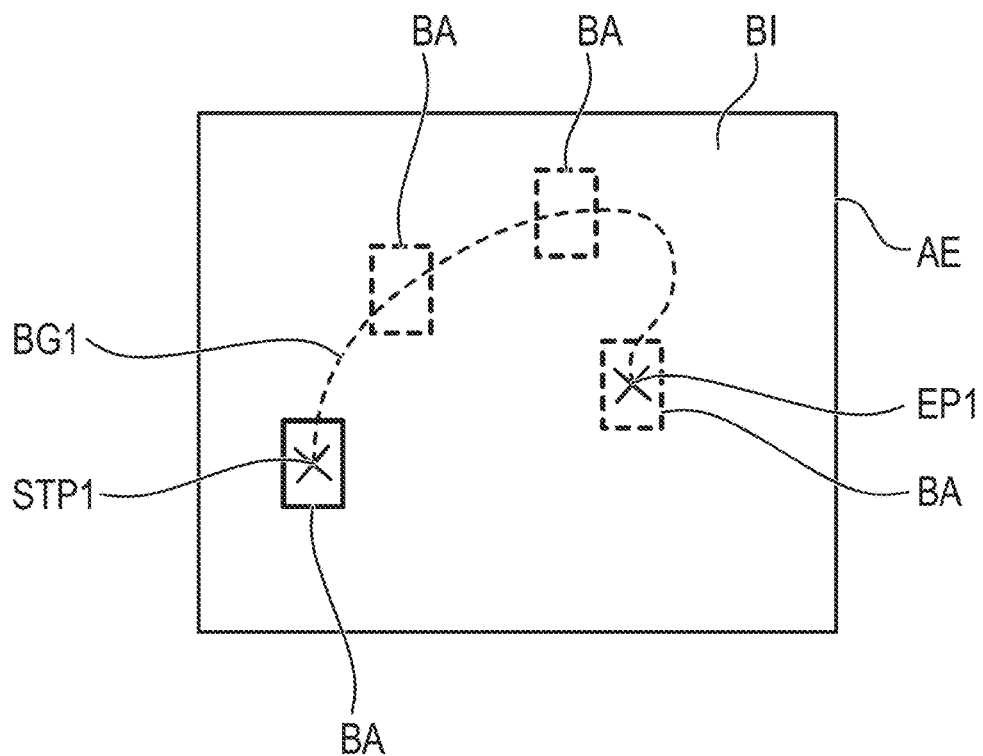
FIG. 2b shows a display unit.
Figure 3:
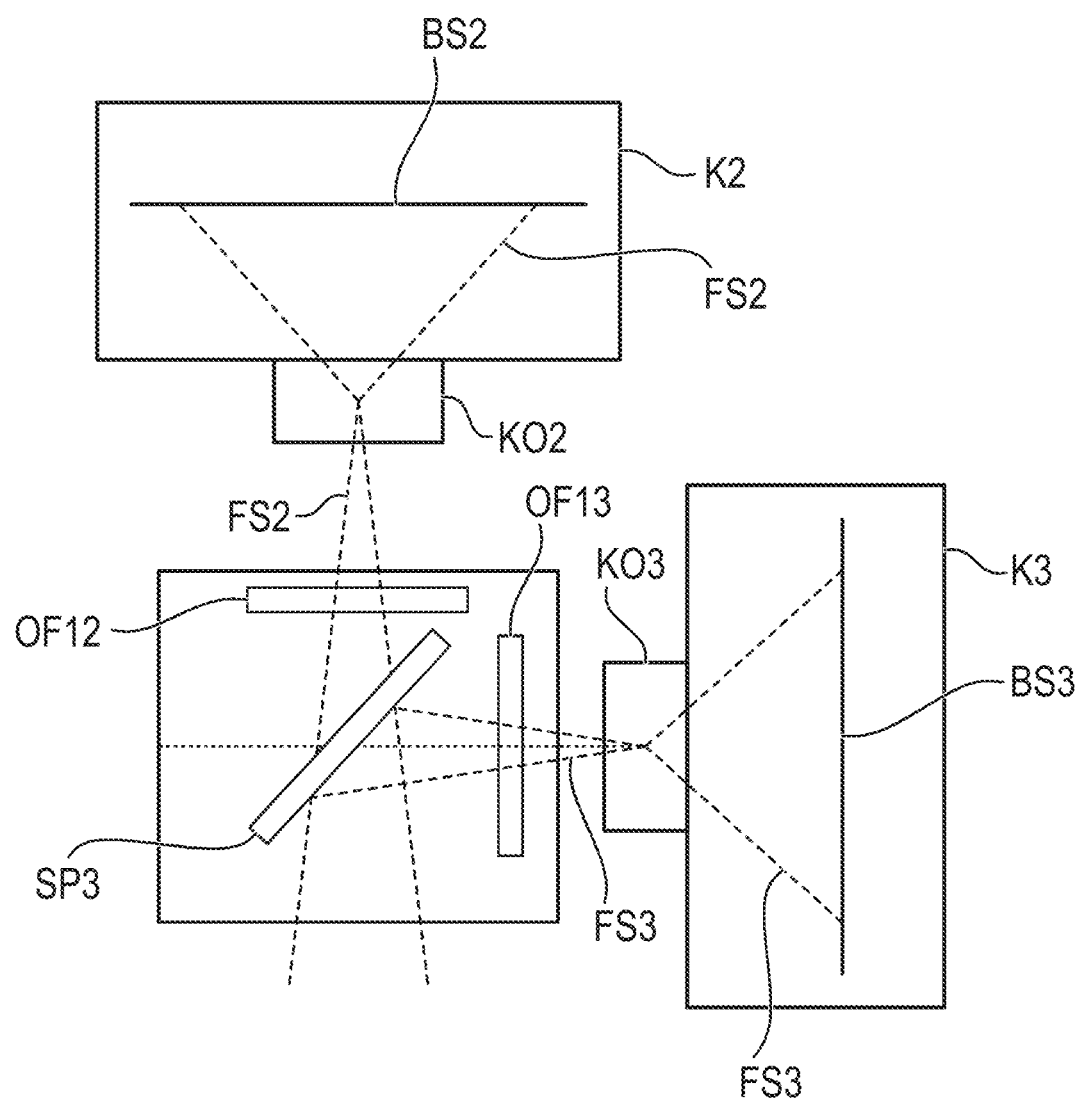
FIG. 3 shows one preferred embodiment of the use of two image sensors.
Figure 4:
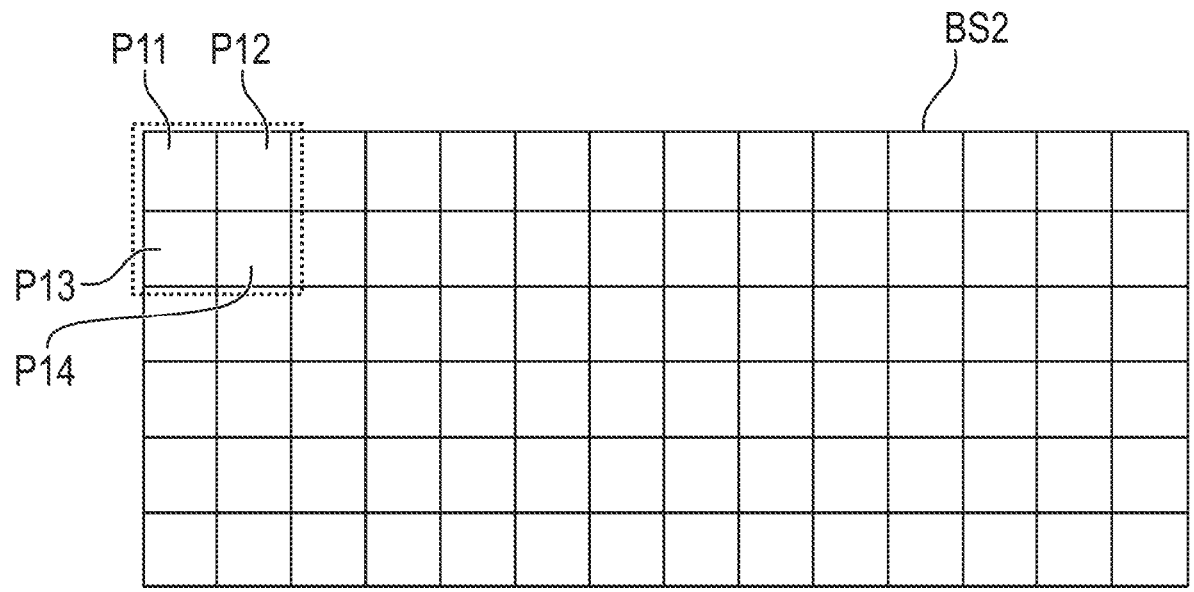
FIG. 4 shows one preferred embodiment of an image sensor having multiple sensor pixels.
Figure 5:
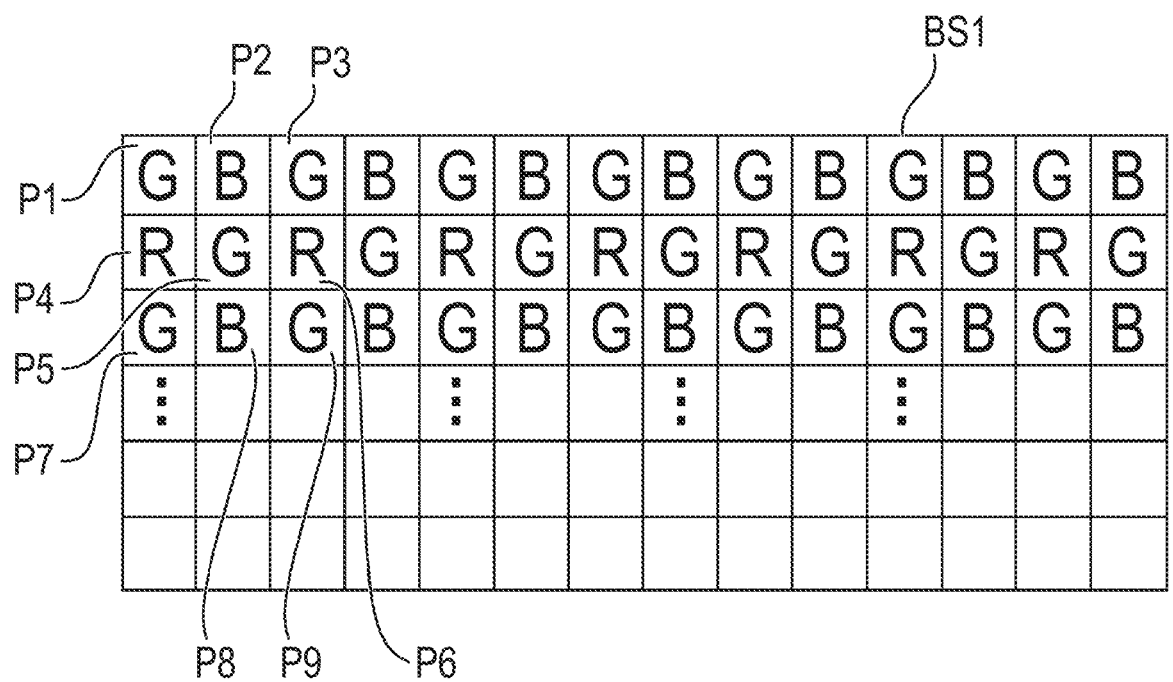
FIG. 5 shows a further preferred embodiment of an image sensor as a colour image sensor having multiple sensor pixels.
Figure 6:
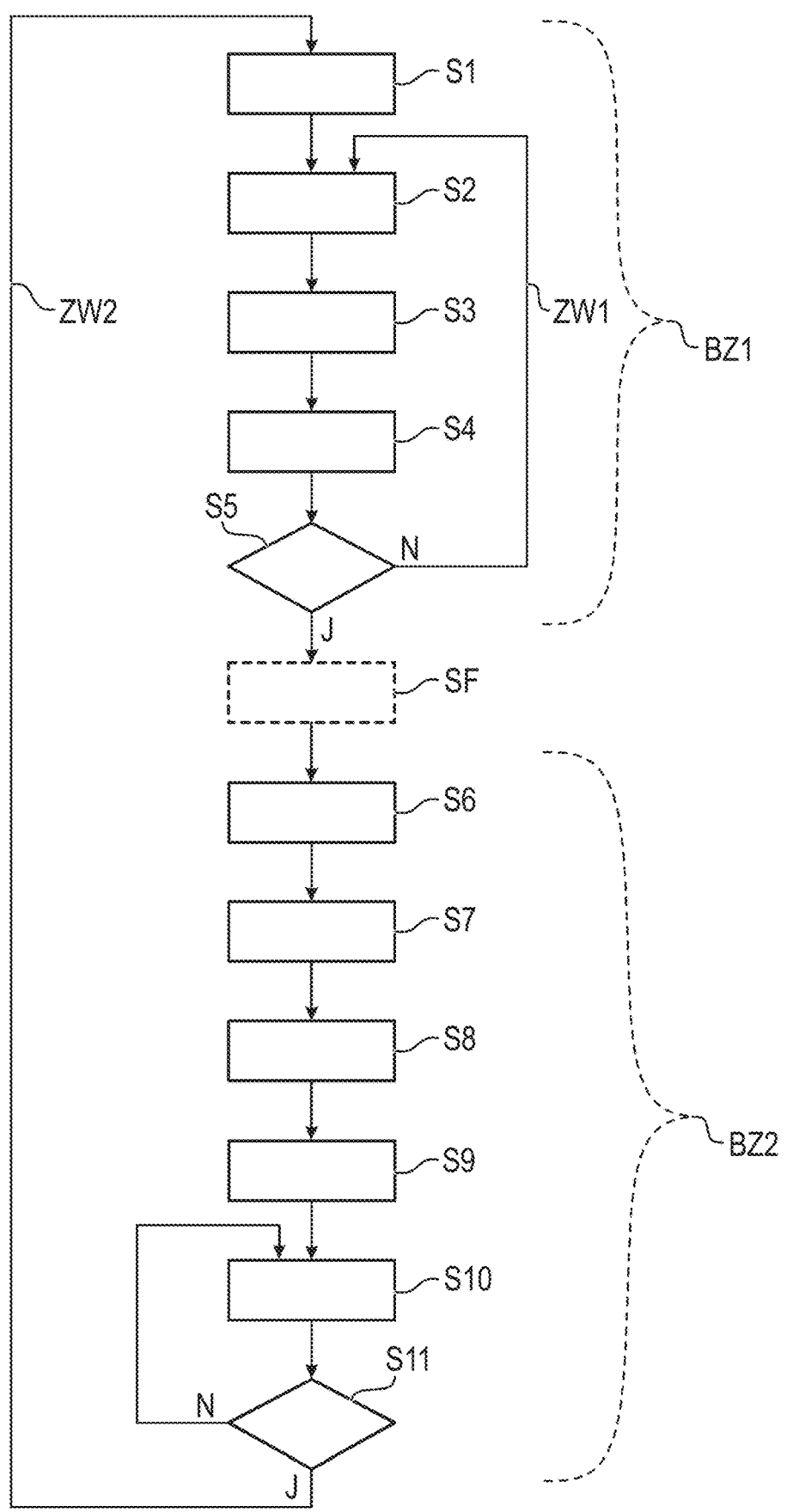
FIG. 6 shows preferred steps in the scope of carrying out a preferred embodiment of the method according to the invention.
Figure 7:
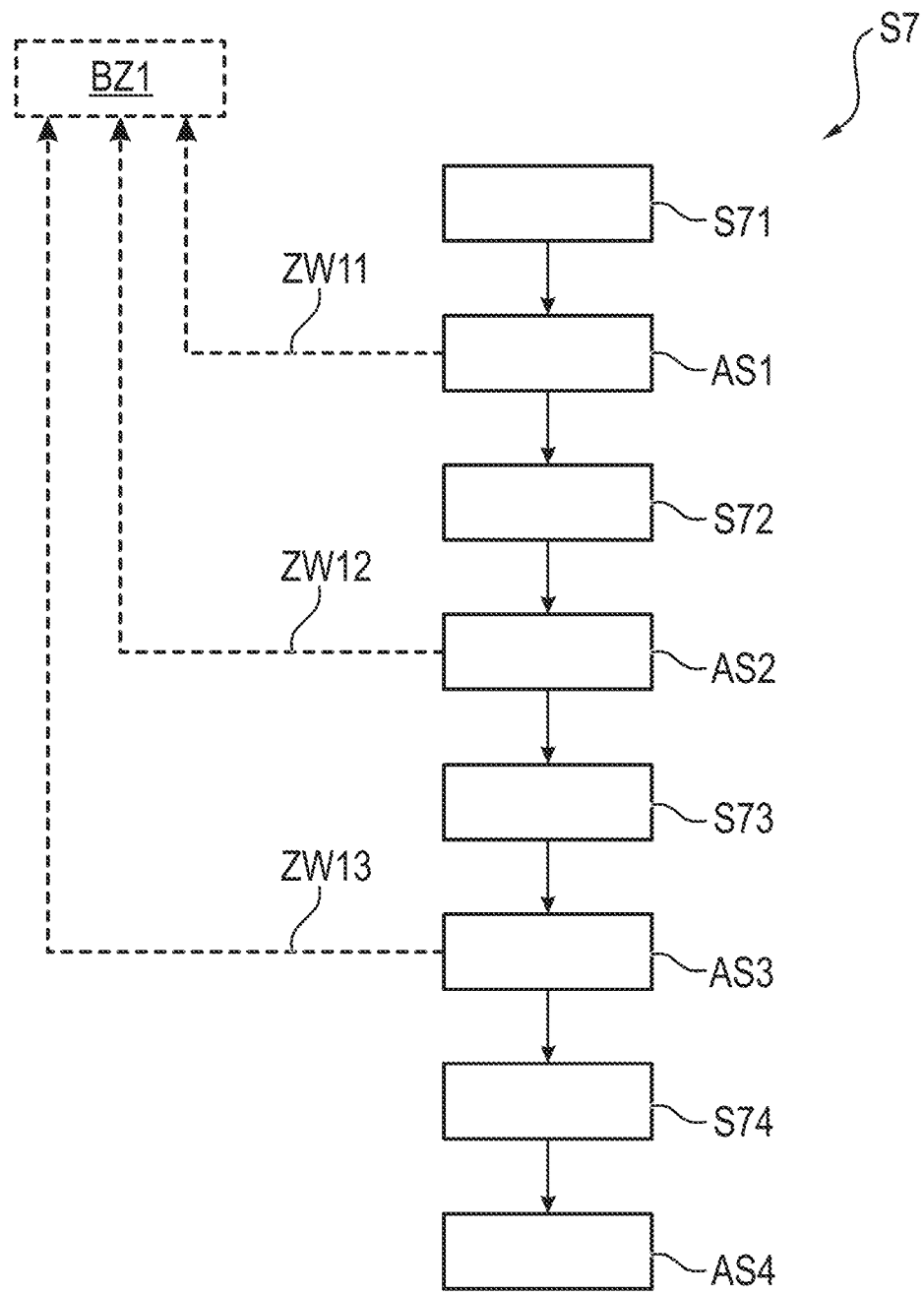
FIG. 7 shows preferred steps for acquiring fluorescent radiation in the second operating state.
Figure 9:
FIG. 9 shows a further detail of the cell image in the second operating state.
Figure 11:
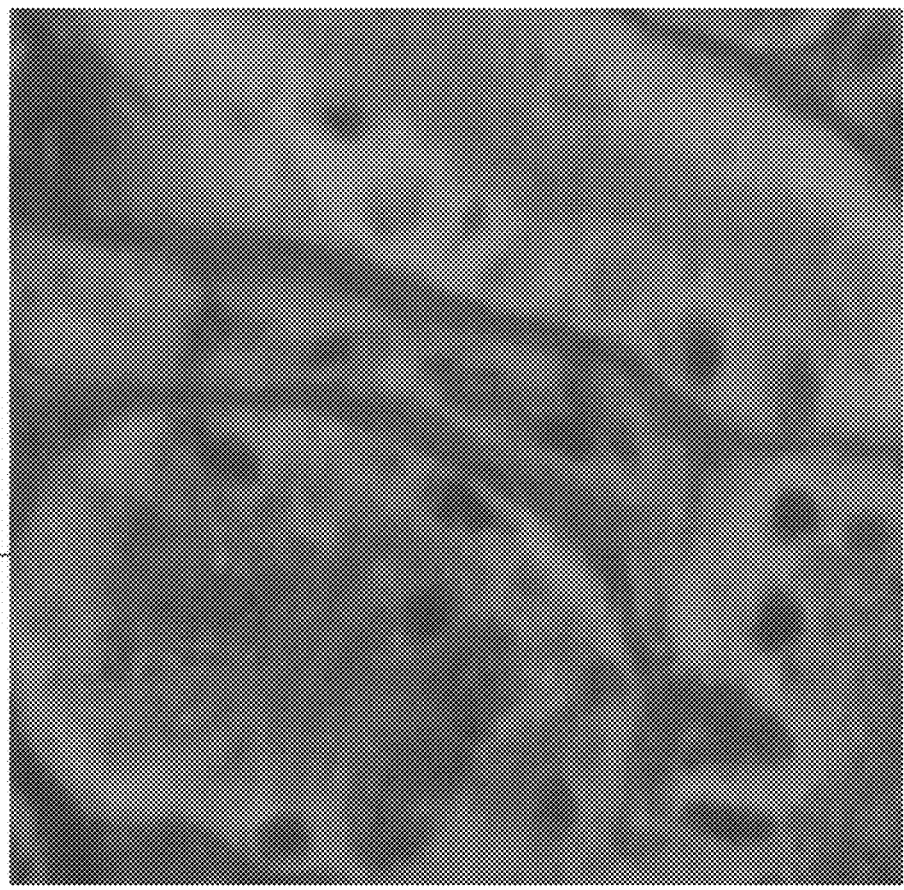
FIG. 11 shows a further digital image having a further detail of the tissue during the second operating state.

The invention is explained in greater detail hereafter on the basis of the figures on the basis of special embodiments without a restriction of the general inventive concept. In the figures:

FIG. 1 shows one preferred embodiment of the device according to the invention,

FIG. 2a shows a user input device,

FIG. 2b shows a display unit,

FIG. 3 shows one preferred embodiment of the use of two image sensors,

FIG. 4 shows one preferred embodiment of an image sensor having multiple sensor pixels, FIG. 5 shows a further preferred embodiment of an image sensor as a colour image sensor having multiple sensor pixels, FIG. 6 shows preferred steps in the scope of carrying out a preferred embodiment of the method according to the invention, FIG. 7 shows preferred steps for acquiring fluorescent radiation in the second operating state, FIG. 8 shows different image details of cell images during a first operating state, FIG. 9 shows a further detail of the cell image in the second operating state, FIG. 10 shows different image details of an immunofluorescence image of a tissue at different points in time during the first operating state, FIG. 11 shows a further digital image having a further detail of the tissue during the second operating state.

FIG. 8a shows a first image detail BI1, in which so-called HEP cells (human epithelial cells) are shown. This image was obtained during a first operating state using the device according to the invention. A user desires, for example, to observe this image detail BI1 in higher image quality. Previously, he has possibly observed another image detail, BI2 from FIG. 8b, and has thus chosen the corresponding image detail by means of a movement gesture, which was input via a user input device, as shown in FIG. 8a.

According to the method according to the invention, an acquisition of the fluorescent radiation is then performed to obtain an image, for example, the image BI3 from FIG. 9, in a second operating state, which has a higher image quality than the images BI1, BI2 from FIG. 8a or 8b, respectively.

A further example is given in FIGS. 10a and 10b, in which the user, during the first operating state, effectuates a relative position change between sample and optical system by means of specification of his movement gesture from an image detail BI12 to an image detail BI11, wherein then after terminating his movement gesture, in the second operating state, an image BI13 is obtained and displayed, as shown in FIG. 11.

A user input device can be, for example, a so-called touchscreen, on which the user carries out the movement gesture by displacing his fingertip on the touchscreen surface. The movement gesture is preferably terminated or is detected as terminated when the user removes the finger from the touchscreen surface. Alternatively, the movement gesture can be detected as terminated when the user, considered over time, no longer or no longer noticeably performs a location change of his fingertip on the touchscreen surface, such that a certain threshold value with respect to a position change of the fingertip is undershot within a predetermined time window. The spatial threshold value relates to the change of the detected position of the finger on the touchscreen.

The user input device can alternatively be an input means, for example a computer mouse, via which the user can input such a movement gesture.

A control unit can then derive or detect a movement gesture in dependence on an input signal acquired by the user input device.

FIG. 1 shows a preferred embodiment of the device V according to the invention, which is designed to carry out the method according to the invention. A sample G, preferably a tissue sample, is provided, for example, inside an object carrier OT. A holding device H is used for holding the object carrier OT and/or the sample G. The holding device H is preferably coupled to a positioning unit P, which is designed to change a relative position between the sample G and an optical system OS. The change of the relative position between the sample G and/or the holding device H and the optical system OS can, alternatively to the variant shown in FIG. 1, also be effectuated in that the optical system OS is changed by a positioning unit in its relative position in relation to the tissue G and/or the holder H.

The optical system OS guides fluorescent radiation FS from the sample G onto an image sensor BS. The optical system OS preferably consists of an objective lens OB and a further optical unit OE, which will be discussed in greater detail hereafter.

The image sensor BS comprises multiple sensor pixels for acquiring fluorescent radiation FS emitted by the sample G. Excitation light or excitation radiation AS is provided by means of an excitation light source AL and the sample G is illuminated in this way. The excitation radiation AS firstly passes an optical filter FI1, which filters out the desired excitation radiation in a defined wavelength range. The radiation AS is then conducted via a dichroic mirror SP1 onto the objective lens OB and/or the sample G.

The fluorescent radiation FS emitted by the sample G is conducted through the objective lens OB back to the dichroic mirror, which guides the fluorescent radiation having its wavelength, which differs from the wavelength of the excitation radiation AS, onto the image sensor. A filter FI2 preferably filters out the fluorescent radiation. The fluorescent radiation FS preferably passes a camera objective lens KO in this case, which then conducts the fluorescent radiation FS onto the image sensor BS of a camera K.

The device V according to the invention comprises at least one control unit S. The control unit S in turn comprises a first interface SC1 to a user input device N. The control unit S receives an input signal ES of the user input device N via the interface SC1 and can derive or determine a movement gesture of a user therefrom and detect both a termination of the movement gesture and also a beginning of a new movement gesture.

The control unit S can output an image signal BS and/or a control signal ST5 to a display unit AE via an interface SC5 and can thus have digital images displayed. The user input device N and the display unit AE can also be provided in a single combined unit, for example, a touchscreen. The display unit can alternatively be a so-called computer monitor, wherein then the user input device N can be a so-called computer mouse. If the user input device N and the display unit AE are unified, the interfaces SC1, SC5 can thus also be unified as a preferably bidirectional interface.

The control unit S receives sensor pixel values SW of the image sensor BS via an interface SC2. Furthermore, the control unit S can transmit one or more control signals ST2 to the camera K via the interface SC2. Such a control signal ST2 can indicate, for example, an acquisition time to be used for acquiring fluorescent radiation by the image sensor BS and/or camera K. Furthermore, such a control signal ST2 can also be a so-called trigger signal, to request an acquisition of fluorescent beams by the image sensor BS at a defined point in time.

The control unit S preferably comprises an interface SC6, via which the control unit S controls, by means of a control signal ST6, the objective lens OB and/or the optical system OS to change an optical setting, for example, a focusing of the optical system OS.

The control unit S can control the excitation light source AL by means of a control signal ST3 via an interface SC3 to turn the excitation light on or off.

Furthermore, the control unit S can turn the laser light source LL on and off and preferably furthermore change its brightness via the interface SC7 by means of a control signal ST7.

The positioning unit P is designed to change at least one lateral position of the sample in the XY direction in relation to the optical system OS. The control unit S can control the positioning unit P via the interface SC4 by means of the control signal ST4 in such a way that a desired change of the relative position between the sample G and/or the holder H in relation to the optical system OS is effectuated.

The positioning unit P is preferably also embodied to change a Z position to change a distance between the sample G and the optical system OS for the purpose of focusing. Laser radiation LS can be used for this purpose in particular, which can then be coupled into the optical system OS via a laser light source LL, preferably using a dichroic mirror SP2, and which can then be acquired in the image sensor BS. In an alternative embodiment, the objective lens is designed to change a distance in the Z direction between the objective lens and the sample G in dependence on the control signal ST6, in order to change a focusing setting.

According to the embodiment shown here, the image sensor BS is a colour image sensor BS1, such that the camera K is a colour camera K1.

FIG. 2a shows an illustration of a user input device N in the form of a touchscreen or a touch-sensitive display unit N1. A user can, for example, carry out a movement gesture BG1 on the touch-sensitive surface BO by placing his finger at a starting point STP1 and guiding the finger along the curve of the movement gesture BG1 onto an endpoint EP1 and then terminating the movement gesture there. Such a termination of a movement gesture can then be detected by the control unit S from FIG. 1.

FIG. 2b shows a display unit AE, which is preferably identical to the user input device N1 of FIG. 2a. Alternatively, the display unit AE can be a so-called computer monitor or display screen in the case in which the user input device is a computer mouse.

The movement gesture BG1 is again shown on the display unit as a dashed line for the orientation of the reader. A defined image detail BA from the immunofluorescence image and/or the sample is then displaced because of the change of the relative position between the positioning system or the positioning unit P and the optical system OS from FIG. 1 along the curve of the movement gesture BG1 onto the endpoint EP1. If the user terminates the movement at this endpoint EP1, a change is then made to the second operating state and an immunofluorescence image is determined therein using the second acquisition duration.

FIG. 2a furthermore shows a further movement gesture BG2, which the user then executes from a starting point STP2, which coincides with the prior endpoint EP1, onto a further endpoint EP2. If such a beginning of a new movement gesture BG2 of the user is detected, the second operating state is thus then preferably terminated and a transition is made back into the first operating state.

FIG. 6 shows steps preferably to be carried out according to one embodiment of the method according to the application. During the first operating state BZ1, a step S1 takes place, in which the excitation light source is switched on, such that the sample is continuously illuminated using the excitation radiation during the first operating state. Preferably, configuration parameters are moreover transmitted by the control unit via the interface SC2 to the camera K in the step S1.

In a step S2, a change of the relative position between the sample and the optical system then takes place in dependence on a detected movement gesture of the user. In this case, the change of the relative position can take place in such a way that firstly only a part of a movement gesture is detected and then the relative position is changed to a certain extent in accordance with this partial movement gesture.

In a step S3, an acquisition of the fluorescent radiation is then performed using the first acquisition duration. This is chosen such that a sufficiently fluid movement of the digital images displayed at the successive points in time is provided. A digital image is then determined by the control unit in step S3 on the basis of the sensor pixel values resulting for the individual sensor pixels.

In a step S4, the digital image is then displayed by means of output on the display unit.

In a step S5, it can then be checked whether the movement gesture of the user has been terminated by the user. If this is not the case, the method thus remains in the first operating state BZ1. This is shown by the branch ZW1 in FIG. 6.

In the first operating state BZ1, an acquisition of the fluorescent radiation as well as the determination and the display of the digital image at successive points in time at a defined repetition frequency thus take place.

However, if it is detected in a step S5 that the movement gesture has been terminated by the user, a change is thus made from the first operating state BZ1 to the second operating state BZ2.

Preferably, between the first operating state BZ1 and the second operating state BZ2, in an optional intermediate step SF before reaching the second operating state BZ2, a focusing of the optical system on the sample is also carried out using laser radiation LS of the laser light source LL from FIG. 1. The laser radiation LS is preferably coupled in by means of a dichroic mirror SP2. Such an autofocusing method using laser light radiation LS is described in greater detail, for example, in the EP patent application number 17 001 037.5 of the applicant. During the procedure of autofocusing, the excitation light source for emitting the excitation radiation is preferably switched off, wherein furthermore the image last determined in the first operating state is preferably continuously displayed on the display unit during the procedure of autofocusing. The impression of "live microscopy" is thus not interrupted for the user during the autofocusing.

In the second operating state BZ2, in a step S6, an illumination of the sample using the excitation radiation and/or switching on of the excitation light source for illuminating the sample using the excitation radiation takes place.

In a step S7, the acquisition of the fluorescent radiation is then performed by means of the multiple sensor pixels using the second acquisition duration, which is preferably greater than the first acquisition duration. On the basis of resulting sensor pixel values of the image sensor, a determination of a further digital image is then performed, which is then displayed in a step S8. In a step S9, a termination of the acquisition of the fluorescent radiation and a termination of the illumination of the sample take place after lapse of the second acquisition duration. The display of the further digital image is performed continuously for the second operating state in a step S10.

Because, in the second operating state BZ2 after the lapse of the second acquisition duration, a further digital image is continuously displayed, and furthermore the illumination of the sample by the excitation radiation is terminated, a so-called burnout of the sample because of illumination using the excitation radiation is minimized. Furthermore, the impression results for the user by way of the method according to the invention that he not only has acquired images as representations of a real microscopic image displayed continuously during the performance of his movement gesture, but rather that also a continuous microscopic image is still displayed during the second operating state, since he has the further digital image continuously displayed. By way of the solution proposed here, the user thus receives the impression of continuous microscopy, although no further images with simultaneous illumination of the tissue by the excitation radiation are obtained.

In a step S11, a check is then performed as to whether a new movement gesture of the user is detected. This can be, for example, the movement gesture BG2 from FIG. 2a.

If this is not the case, the sequence thus returns to step S10 and the further digital image is furthermore continuously displayed in the second operating state BZ2. However, if this is the case, the second operating state is thus terminated and a transition is made into the first operating state BZ1. This is shown by the branch ZB2 in FIG. 6.

In this way, the user can firstly move a first image detail in the displayed image by his first movement gesture BG1 from FIG. 2a, to then have this image detail displayed in higher image quality in the second operating state after a termination of the movement gesture. However, the user can furthermore return into the first operating state by beginning the second movement gesture and choosing a new image detail by means of the second movement gesture.

In the preferred embodiment of the proposed method described here with reference to FIG. 6, the change of the relative position in step S2, the acquisition of the fluorescent radiation in step S3, and the display of the digital image in step S4 take place in the form that steps S2, S3, and S4 all follow one another serially. In an alternative embodiment, the change of the relative position can be carried out continuously, while the acquisition of the fluorescent radiation and the display of the digital image take place parallel in time to the change of the relative position. Steps S3 and S4 would then follow one another in time, for example, but this sequence of steps S3 and S4 would be executed in parallel to step S2.

A variant of step S7 for acquiring the fluorescent radiation in the second operating state is shown in FIG. 7, in which temporary digital images are determined for respective partial acquisition durations, wherein furthermore the further digital image of the second operating state to be displayed is determined on the basis of the temporary digital images.

Steps S71 to AS4 are carried out in the second operating state during the second acquisition duration to acquire the emitted fluorescent radiation.

Firstly, in a step S71, during a partial acquisition duration of, for example, 19 ms, a first temporary digital image is determined and displayed in a display step AS1. In a next method step S72, a further temporary digital image is then determined using a partial acquisition duration of 19 ms and the further digital image is determined as the mean value of the two temporary digital images from steps S71 and S72 and displayed in step AS2. During an acquisition step S73, an acquisition of the emitted fluorescent radiation then occurs using the partial acquisition duration of 19 ms to obtain and/or determine a third temporary digital image, wherein the further digital image is then determined from the three temporary digital images by means of averaging of the pixel values. The further digital image is then displayed in the third display step AS3. This is then performed accordingly in an acquisition step S74 and a display step AS4, such that in this exemplary embodiment, four temporary digital images are determined and the further digital image is determined on the basis of the temporary digital images and then displayed. In this exemplary embodiment, the second acquisition duration consists of four partial acquisition durations.

Such a method for determining the further digital image on the basis of multiple temporary digital images is advantageous since sensor noise or a noise signal overlaid on the image signals is reduced or minimized as a result of its statistical properties by the averaging of the temporary digital images, but at the same time the actual intensity or signal intensity of the fluorescent radiation as a useful signal is maintained.

Branches ZW11, ZW12, ZW13 away from the corresponding steps AS1, AS2, AS3 each illustrate a possible termination of the determination of the temporary digital images in the case in which a beginning of a new movement gesture of the user is detected in the second operating state. The acquisition of the emitted fluorescent radiation in the second operating state is then also terminated and a transition is made into the first operating state BZ1. This embodiment is advantageous since it is thus possible for the user to begin a new movement gesture already during the averaging of the temporary digital images, before the entire second acquisition duration accumulated from partial acquisition durations has passed. If the further digital image were obtained in the second operating state using a single, overall, uninterrupted second acquisition duration, the user thus could only effectuate a change of the relative position and/or a selection of an image detail by beginning a new movement gesture when the entire second acquisition duration has passed. According to the preferred solution here from FIG. 7, however, the user can already change the change of the relative position and/or the choice of the image detail before lapse of the second acquisition period of time because of the averaging procedure which is carried out of the temporary digital images and the option of terminating the second operating state. The further digital image is determined continuously from the temporary digital images and its display on the display unit is updated after each of the corresponding; in this way, an image of an image quality is displayed to the user already before lapse of the entire second acquisition duration, which is better than the image quality of a digital image during the first operating state. In particular, the user would thus have an image continuously improving in its image quality progressively displayed during the passage of time until finally the second acquisition duration has passed.

According to FIG. 1, a so-called colour camera K1 having an image sensor BS1 as the image sensor BS can be used as the camera K. According to an alternative embodiment from FIG. 3, a camera K2 having a greyscale image sensor BS2, which detects the fluorescent radiation FS, FS2 in a green channel, can be used as the camera K. For this purpose, a so-called green channel of the fluorescent radiation FS2 can be selected by means of an optical filter OF12 and then supplied to the greyscale image sensor BS2. This preferably again takes place via a camera objective lens KO2.

In relation to the use of a single greyscale image sensor, the use of a colour image sensor has the advantage that not only fluorescent radiation as a result of the fluorescence of the previously introduced fluorescent pigment becomes visible in the image, but rather that also a so-called autofluorescence of the tissue can be acquired and displayed in a further channel, for example, in a red channel. This can be, for example, colourations having a brown component. Such an item of additional image information can provide additional items of optical information with respect to the displayed tissue to the user by way of the use of a colour image sensor.

According to one preferred embodiment according to FIG. 3, the device can furthermore comprise a further greyscale image sensor BS3, which preferably detects fluorescent radiation in a red channel, in addition to the greyscale image sensor BS2. For this purpose, the fluorescent radiation FS of the tissue can be divided by means of the dichroic mirror SP3 such that the fluorescent radiation FS3 represents the red channel. In this case, an optical filter OF13 can select and/or transmit the red channel. The information or colour information of the two greyscale image sensors BS2 and BS3 can then be overlaid and/or combined by the control unit S.

FIG. 4 shows a greyscale image sensor BS2, which comprises pixels P11, P12, P13, P14. The greyscale image sensor BS2 can be subjected with its pixel resolution or pixel number per unit of area to so-called "binning", by adding up the pixel values of the pixels P12, P12, P13, P14, wherein then a fourfold area in relation to the area of one sensor pixel is used for an individual image pixel BP. In this way, a reduction of the resolution in the resulting digital image by a factor of 4 results in relation to the resolution of the image sensor BS2.

FIG. 5 shows an example of a colour image sensor BS1, which comprises different pixels P1, . . . , P9, wherein the corresponding colours G, B, R respectively indicate whether a green (G), blue (B), or red (R) colour filter is present in front of the respective pixel P1, . . . , P9. For the colour pixel P5, an item of RGB colour image information having three colour channels can be obtained, for example, in that so-called "debayering" is carried out. In this case, for the pixel P5, an item of red information is obtained on the basis of the pixel values of the pixels P4 and P6, an item of green information is obtained on the basis of the sensor pixel values of the pixels P1, P3, P5, P7, and P9, and an item of blue information is obtained on the basis of the pixel values of the pixels P8 and P2. In this way, an item of three channel colour information as the red, green, and blue channels may thus be obtained for each individual pixel P1, . . . , P9, without causing a resolution reduction in the resulting image with respect to the pixel number or pixel density per unit of area in relation to the image sensor. If one combined RGB information obtained on the basis of the sensor pixels P1, . . . , P9 in a single image pixel, which corresponds to the area of all the sensor pixels P1, . . . , P9, this would thus additionally correspond to a resolution reduction, namely by the factor 9, in addition to the effect of the debayering. If one were to accordingly use the sensor pixels P1, P2, P3, P4 of the sensor BS1 from FIG. 5 by way of a debayering not only to obtain an item of RGB information but rather also combine them in area, a resolution reduction by a factor of 4 would thus be caused by such a debayering, similarly to binning of the sensor pixels P11, . . . , P14 from FIG. 4.

To determine image pixel values of a digital image from sensor pixel values, the sensor pixel values can also be increased by an amplifier by an amplification factor, wherein such an amplification not only increases the useful signal of the sensor pixels, however, but rather also a noise signal, for example, a sensor noise.

In summary, it can be established that in dependence on the choice of the image sensor, which can be a greyscale sensor or a colour sensor, and in dependence on an image repetition frequency to be sought, different parameters can be chosen differently to determine a digital image from the sensor pixel values:

amplification factor for sensor pixel values,
number of sensor pixel values which are combined by means of binning to form one image pixel value,
number of sensor pixel values which are combined by means of debayering to form one image pixel value.

The digital image in the first operating state and the further digital image in the second operating state are preferably determined such that at equal light intensity of the fluorescent radiation, the digital image of the first operating state and the further digital image of the second operating state have an equal intensity.

The digital image is preferably determined in this case in the first operating state such that it has a first image resolution, wherein the further digital image in the second operating state is determined that it has a second image resolution, and wherein the first image resolution is chosen smaller than the second image resolution.

EXAMPLES

Examples are cited hereafter which permit a person skilled in the art to choose the different parameters such that one or more embodiments of the method described here are achieved.

In a first example, it is assumed that only one greyscale image sensor having a sensor resolution of 2448×2048 pixels is used. In the first operating state, 16 pixels at a time can then jointly be combined via binning to obtain one image pixel. The first acquisition duration can then be 19 ms, such that an image repetition rate of approximately 53 images per second is achieved. Preferably, no amplification of the sensor pixel values is performed. The resulting image then has a resolution of 615×512 pixels in the first operating state. In the second operating state, 300 ms can then be used as a continuous second acquisition duration, which would correspond to an image repetition rate of only 3 images per second. No amplification and preferably also no binning of the sensor pixel values is also performed here. The resulting image then has a resolution of 2448×2048 pixels in the first operating state. The intensity values would then be equal in the first and the second operating state of the first example at equal intensity of the fluorescent radiation.

In a second example, it is assumed that a colour image sensor having a sensor resolution of 2448×2048 pixels is used. In the first operating state, 4 pixels at a time can then be combined jointly via debayering to obtain an image pixel together with a resolution reduction by a factor of 4. The first acquisition duration can then be 19 ms, such that an image repetition rate of approximately 53 images per second is achieved. An amplification of the sensor pixel values by a linear factor 300/19 is preferably performed. The resulting image then has a resolution of 1224×1024 pixels in the first operating state. In the second operating state, 300 ms can then be used as a continuous second acquisition duration, which would correspond to an image repetition rate of only 3 images per second. Preferably no amplification of the sensor pixel values is also performed here. Each nine sensor pixel values are then combined by means of debayering to determine an item of RGB information of one single pixel without causing a resolution reduction. The resulting image then has a resolution of 2448×2048 pixels in the first operating state. The intensity values would then be equal in the first and the second operating state of the second example at equal intensity of the fluorescent radiation.

Alternatively, in the second example, in the second operating state, temporary digital images having respective partial acquisition durations of 19 ms can be obtained and the further digital image can be obtained by averaging the temporary digital images. An amplification of the sensor pixel values by a linear factor of 300/19 is then performed. Each nine sensor pixel values are then combined by means of debayering to determine an item of RGB information of one single pixel without causing a resolution reduction. The resulting image then has a resolution of 2448×2048 pixels in the first operating state. The intensity values would then also be equal here in the first and the second operating state of the second example at equal intensity of the fluorescent radiation.

FIGS. 8 and 9 show exemplary images of immunofluorescence images of HEP cells, which were originally obtained by means of a colour image sensor. The fluorescent pigment used was in this case fluorescein isothiocyanate (FITC). The fluorescent radiation was acquired by means of a CMOS sensor. The power density of the excitation radiation was 65 mW/mm$^2$. In the first operating state, the acquisition duration was approximately 5.07 ms, the amplification was approximately 32.5 dB, and debayering was carried out using each 4 pixels and simultaneous resolution reduction, such that the image resolution corresponded to ¼ (one quarter) of the image resolution of the second operating state. In the second operating state, the acquisition duration was approximately 162.12 ms, the amplification was approximately 2.4 dB, and debayering was carried out with each 9 pixels without resolution reduction, such that the image resolution corresponded to the fourfold image resolution of the first operating state. For both operating states, an equal image intensity was achieved at equal intensity of the fluorescent radiation.

FIGS. 10 and 11 show exemplary images of immunofluorescence images of tissue parts of a rat liver, which were originally obtained by means of a colour image sensor. In the first operating state, the acquisition duration was approximately 8.93 ms, the amplification was approximately 10.92 dB, and debayering was carried out using each 4 pixels and simultaneous resolution reduction, such that the image resolution corresponded to ¼ (one quarter) of the image resolution of the second operating state. In the second operating state, the acquisition duration was approximately 142.8 ms, the amplification was approximately 35.00 dB, and debayering was carried out with each 9 pixels without resolution reduction, such that the image resolution corresponded to the fourfold image resolution of the first operating state. For both operating states, an equal image intensity was achieved at equal intensity of the fluorescent radiation.

The features disclosed in the preceding description, the embodiments, and the drawings can be significant both individually and also in any arbitrary combination for the implementation of exemplary embodiments in the various designs thereof here and can be combined with one another arbitrarily—if not indicated to the contrary in the description.

Although some aspects were described in conjunction with a device, it is apparent that these aspects also represent a description of the corresponding method, such that a block or a component of a device is also to be understood as a corresponding method step or as a feature of a method step. Similarly thereto, aspects which were described in conjunction with a method step or as a method step also represent a description of a corresponding block or detail or feature of a corresponding device.

Depending on the defined implementation requirements, exemplary embodiments of the invention can be implemented in hardware or software, in particular the control unit mentioned here. The implementation can be carried out using a digital storage medium, for example, a floppy disk, a DVD, a Blu-Ray disk, a CD, a ROM, a PROM, an EPROM, an EEPROM, or a FLASH memory, a hard drive or another magnetic or optical memory, on which electronically readable control signals are stored, which can cooperate or do cooperate with a programmable hardware component in such a way that the respective method is carried out.

A programmable hardware component such as the control unit mentioned here can be formed by a processor, a computer processor (CPU=Central Processing Unit), a graphics processor (GPU=Graphics Processing Unit), a computer, a computer system, an application-specific integrated circuit (ASIC), an integrated circuit (IC), a one-chip system (SOC=System on Chip), a programmable logic element, or a field-programmable gate array (FPGA) having a microprocessor.

The digital storage medium can therefore be machine-readable or computer-readable. Some exemplary embodiments thus comprise a data carrier, which has electronically readable control signals, which are capable of cooperating with a programmable computer system or a programmable hardware component in such a way that one of the methods described here is carried out. One exemplary embodiment is thus a data carrier (or a digital storage medium or a computer-readable medium), on which the program for carrying out one of the methods described herein is recorded.

In general, exemplary embodiments of the present invention can be implemented as a program, firmware, computer program, or computer program product having a program code or as data, wherein the program code or the data is/are capable of carrying out one of the methods when the program runs on a processor or a programmable hardware component. The program code or the data can also be stored, for example, on a machine-readable carrier or data carrier. The program code or the data can be provided, inter alia, as source code, machine code, or byte code and also as another intermediate code.

A program according to one exemplary embodiment can implement one of the methods as it is carried out, for example, in that it reads out storage points or writes one datum or multiple data therein, whereby possibly switching procedures or other procedures in transistor structures, in amplifier structures, or in other electrical, optical, magnetic components or components operating according to another functional principal are effectuated. Accordingly, data, values, sensor values, or other items of information can be acquired, determined, or measured by a program by reading out a storage point. A program can therefore acquire, determine, or measure variables, values, measured variables, and other items of information by reading out one or more storage points, and can effectuate, prompt, or carry out an action and also control other devices, machines, and components by writing in one or more storage points.

The above-described exemplary embodiments merely represent an illustration of the principles of the present invention. It is self-evident that modifications and variations of the arrangements and details described herein will be clear to other persons skilled in the art. It is therefore intended that the invention is solely restricted by the scope of protection of the following embodiments and not by the specific details which were presented herein on the basis of the description and the explanation of the exemplary embodiments.

The invention claimed is:

1. A method for acquiring and displaying an immunofluorescence image of a biological sample, the method comprising, in a first operating state:
   continuously illuminating the biological sample using excitation radiation,
   changing a relative position between the biological sample and an optical system, which guides fluorescent radiation emitted by the biological sample onto at least one image sensor, in dependence on a movement gesture of a user,
   acquiring the fluorescent radiation by multiple sensor pixels of the at least one image sensor using a first acquisition duration and determining a digital image, and
   displaying the digital image,
   wherein, in the first operating state, the acquisition of the fluorescent radiation as well as the determination and the display of the digital image are repeated at successive points in time at a defined repetition frequency,
   wherein, upon detection of a termination of the movement gesture, a change is made from the first operating state to a second operating state,
   the method further comprising, in the second operating state:
   illuminating the biological sample using the excitation radiation,
   acquiring the fluorescent radiation emitted by the biological sample by the multiple sensor pixels using a second acquisition duration and determining a further digital image,
   displaying the further digital image,
   terminating the acquisition of the emitted fluorescent radiation and terminating the illumination of the biological sample after lapse of the second acquisition duration, and
   continuously displaying the further digital image after the termination of the acquisition of the fluorescent radiation and the termination of the illumination of the biological sample.

2. The method according to claim 1, wherein the second acquisition duration is greater than the first acquisition duration.

3. The method according to claim 1, further comprising:
   terminating the second operating state and changing to the first operating state upon detection of a beginning of a new movement gesture of the user.

4. The method according to claim 1, wherein the digital image in the first operating state and the further digital image in the second operating state are determined such that at equal light intensity of the fluorescent radiation, the digital image of the first operating state and the further digital image of the second operating state have an equal intensity.

5. The method according to claim 4, wherein the digital image in the first operating state and the further digital image in the second operating state are determined such that at equal light intensity of the fluorescent radiation, the digital image of the first operating state and the further digital image of the second operating state have an equal intensity, by one or more of the following parameters being chosen differently for the first operating state and for the second operating state:
   an amplification factor for sensor pixel values,
   a number of sensor pixel values which are combined by binning to form one image pixel value, and
   a number of sensor pixel values which are combined by debayering to form one image pixel value.

6. The method according to claim 1, wherein the digital image is determined in the first operating state such that the digital image has a first image resolution, wherein the further digital image is determined in the second operating state such that the further digital image has a second image resolution, and wherein the first image resolution is chosen smaller than the second image resolution.

7. The method according to claim 1, wherein, in the second operating state, the acquisition of the emitted fluorescent radiation is carried out using multiple successive partial acquisition durations within the second acquisition duration, wherein corresponding temporary digital images are determined for the partial acquisition durations, and wherein the further digital image is determined on the basis of the corresponding temporary digital images.

8. The method according to claim 7, wherein, in the second operating state, upon detection of a beginning of a new movement gesture of the user, the acquisition of the emitted fluorescent radiation and the determination of the corresponding temporary digital images is terminated, and a transition is made into the first operating state.

9. The method according to claim 1, wherein a colour image sensor is used as the image sensor.

10. The method according to claim 1, wherein a greyscale image sensor, which detects fluorescent radiation in a green channel, is used as the image sensor.

11. The method according to claim 10, wherein a further greyscale image sensor is used, which detects fluorescent radiation in a red channel.

12. The method according to claim 1, wherein, upon a change from the first operating state to the second operating state, before reaching the second operating state, a focusing of the optical system on the biological sample is carried out.

13. A device for acquiring and displaying an immunofluorescence image of a biological sample, the device comprising:
- an excitation light source for illuminating a biological sample, using excitation radiation,
- a holding device for holding the biological sample,
- at least one image sensor, having multiple sensor pixels for acquiring fluorescent radiation emitted by the biological sample, an optical system for guiding the fluorescent radiation from the biological sample onto the image sensor,
- a positioning unit, which is designed to change a relative position between the biological sample and the optical system, and
- at least one control unit, having
  - a first interface to a user input device,
  - a second interface to the image sensor,
  - a third interface to the excitation light source,
  - a fourth interface to the positioning unit, and
  - a fifth interface to a display unit,
- wherein the control unit is designed, in a first operating state,
  - to control the excitation light source in such a way that the sample is continuously illuminated using the excitation radiation,
  - to derive a movement gesture of the user from an input signal of the user input device and to control the positioning unit in such a way that the relative position between the biological sample and the optical system is changed in dependence on the movement gesture,
  - to control the image sensor in such a way that, by the multiple sensor pixels, the fluorescent radiation is acquired using a first acquisition duration and furthermore to determine a digital image from resulting sensor pixel values, and also furthermore
  - to control the display unit to display the digital image,
- wherein the control unit is further designed, in the first operating state,
  - to repeat the acquisition of the fluorescent radiation as well as the determination and the display of the digital image at successive points in time using a defined repetition frequency, and
  - upon detection of a termination of the movement gesture, to change to a second operating state,
- wherein the control unit is further designed, in the second operating state,
  - to control the image sensor so that, by the multiple sensor pixels, the fluorescent radiation is acquired using a second acquisition duration,
  - to determine a further digital image from resulting sensor pixel values,
  - to control the display unit to display the further digital image,
  - to control the image sensor so that after lapse of the second acquisition duration, the acquisition of the fluorescent radiation is terminated,
  - to control the excitation light source in such a way that the illumination of the sample is terminated after lapse of the second acquisition duration, and
  - to control the display unit after the termination of the illumination of the sample and after the termination of the acquisition of the emitted fluorescent radiation in such a way that the further digital image is continuously displayed.

14. The device according to claim 13, wherein the second acquisition duration is greater than the first acquisition duration.

15. The device according to claim 13, wherein the control unit is further designed, upon detection of a beginning of a new movement gesture of the user, to end the second operating state and to change to the first operating state.

16. The device according to claim 13, wherein the at least one image sensor is a colour image sensor.

17. The device according to claim 13, wherein the at least one image sensor is a greyscale image sensor, which detects fluorescent radiation in a green channel.

18. The device according to claim 17, wherein the device further comprises an additional greyscale image sensor, which detects fluorescent radiation in a red channel.

19. The device according to claim 13, wherein the digital image in the first operating state and the further digital image in the second operating state are determined by one or more of the following parameters:
- an amplification factor for sensor pixel values,
- a number of sensor pixel values which are combined by binning to form one image pixel value, and
- a number of sensor pixel values which are combined by debayering to form one image pixel value,
- wherein each parameter is chosen differently for the first operating state and the second operating state, and
- wherein, at equal light intensity of the fluorescent radiation, the digital image and the further digital image have the equal intensity.

20. The device according to claim 13, wherein the digital image is determined in the first operating state such that the digital image has a first image resolution, wherein the further digital image is determined in the second operating state such that the further digital image has a second image resolution, and wherein the first image resolution is chosen smaller than the second image resolution.

* * * * *